(12) United States Patent
Chang et al.

(10) Patent No.: US 8,168,596 B2
(45) Date of Patent: May 1, 2012

(54) USE OF CYCLOARTANE COMPOUNDS FOR TREATING ARTHRITIS

(75) Inventors: Wen-Liang Chang, Taipei (TW); Tsu-Chung Chang, Taipei (TW); Hang-Ching Lin, Taipei (TW); Yuan Yang, Taipei (TW); Shu-Fen Huang, Taipei (TW)

(73) Assignee: NuLiv Holding Inc., Taipei (TW)

( * ) Notice: Subject to any disclaimer, the term of this patent is extended or adjusted under 35 U.S.C. 154(b) by 558 days.

(21) Appl. No.: 12/253,779

(22) Filed: Oct. 17, 2008

(65) Prior Publication Data

US 2010/0099637 A1    Apr. 22, 2010

(51) Int. Cl.
*A61K 31/56* (2006.01)
*A01N 45/00* (2006.01)

(52) U.S. Cl. .......................................... 514/26; 514/169
(58) Field of Classification Search ................ 514/26, 514/169
See application file for complete search history.

(56) References Cited

U.S. PATENT DOCUMENTS 7,846,904 B2 * 12/2010 Harley et al. ................... 514/26

OTHER PUBLICATIONS

Bagge, et al, "A Longitudinal Study of the Occurrence of Joint Complaints in Elderly People", Age and Ageing 1992,21:160-167.
Kitagawa, et al, Saponin and Sapagenol. XXXIV.[1)] Chemical Constituents of Astragali Radix, the Root of *Astragalus membranaceus* Bunge 91). Cycloastragenol, the 9, 19-Cyclolanostane-type Aglycone of Astragalosides, and the Artifact Aglycone Astragenol, Chem. Pharm Bull. 31(2) 689-697 (1983).
Kitagawa, et al, "Saponin and Sapogenol. XXXV.[1)] Chemical Constituents of Astragali Radix, the Root of *Astragalus membranaceus* Bunge. (2). Astragalosides I, II and IV, Acetylastragaloside I and Isaostragalosides I and II", Chem. Pharm. Bull. 31(2) 698-708 (1983).
Kitagawa, et al, "Saponin and Sapogenol. )(XXVI.[1)] Chemical Constituents of Astragali Radix, the Root of *Astragalus membranaceus* Bunge. (3). Astragalosides III, V and VI", Chem. Pharm. Bull. 31(2) 709-715 (1983).
Osiri, et al, "Specific Cyclooxygenase 2 Inhibitors: A New Choice of Nonsteroidal Anti-Inflammatory Drug Therapy", 1999 American College of Rheumatology, vol. 12, No. 5, Oct. 1999.
Van Saase, et al,"Epidemiology of Osteoarthritis: Zoetermeer survey. Comparison of radiological osteoarthritis in a Dutch population with that in 10 other populations", Annals of the Rheumatic Diseases, 1989; 48, 271-280.

* cited by examiner

*Primary Examiner* — Elli Peselev
(74) *Attorney, Agent, or Firm* — Occhiuti Rohlicek & Tsao LLP

(57) ABSTRACT

A method of treating a disease associated with cartilage defect in a subject in need thereof by administering to the subject an effectively amount of a cycloartane compound of Formula (I).

16 Claims, 8 Drawing Sheets

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: Artificial Primer

<400> SEQUENCE: 1
actctggagt aatgtcacac ct                                                 22

<210> SEQ ID NO 2
<211> LENGTH: 22
<212> TYPE: DNA
<213> ORGANISM: Artificial
<220> FEATURE:
<223> OTHER INFORMATION: Artificial Primer

<400> SEQUENCE: 2
gttggtccac ctttcatctt ca                                                 22

<210> SEQ ID NO 3
<211> LENGTH: 20
<212> TYPE: DNA
<213> ORGANISM: Artificial
<220> FEATURE:
```

-continued

```
<223> OTHER INFORMATION: Artificial Primer

<400> SEQUENCE: 3
aattccgacc tcgtcatcag                                              20

<210> SEQ ID NO 4
<211> LENGTH: 20
<212> TYPE: DNA
<213> ORGANISM: Artificial
<220> FEATURE:
<223> OTHER INFORMATION: Artificial Primer

<400> SEQUENCE: 4
tgcagttttc cagcaatgag                                              20

<210> SEQ ID NO 5
<211> LENGTH: 20
<212> TYPE: DNA
<213> ORGANISM: Artificial
<220> FEATURE:
<223> OTHER INFORMATION: Artificial Primer

<400> SEQUENCE: 5
tggtatcgtg gaaggactca                                              20

<210> SEQ ID NO 6
<211> LENGTH: 23
<212> TYPE: DNA
<213> ORGANISM: Artificial
<220> FEATURE:
<223> OTHER INFORMATION: Artificial Primer

<400> SEQUENCE: 6
agtgggtgtc gctgttataa agc                                          23
```

USE OF CYCLOARTANE COMPOUNDS FOR TREATING ARTHRITIS

BACKGROUND OF THE INVENTION

*Astragalus membranaceous*, a perennial grown in Northern China, attains a height of about 20 feet. Substances in its roots stimulate the immune system. *A. membranaceous*, classified in traditional Chinese medicine as an enhancer of the functions of spleen and lung. It is used not only as a holistic tonic but also for treating edema, reducing excessive perspiration, purging toxins, and promoting tissue healing.

Osteoarthritis (OA), also known as degenerative arthritis, is a type of arthritis characterized by chronic degeneration of the cartilage in the joints, causing severe pain. OA is most commonly found in joints of hands, hips, knees and spine. Development of OA has been attributed to various factors, e.g., age, gender, heredity, stress, and overweight. See David et al., *Arthritis & Rheumatism*, 1998, 41(8): 1343-1355; BAGGE et al, *Age Ageing*, 1992; 21: 160-167; Van Saase J L C M, et al., *Ann Rheum Dis* 1989; 48:271-80. In addition, matrix metalloproteinases (MMPs), a family of zinc-dependent endopeptidases that degrades collagen, have been found to contribute to OA development.

Traditionally, OA is treated with either pain relievers (e.g., aspirin) or nonsteroidal anti-inflammatory drugs (e.g., diclofenac, ibuprofen and naproxen), which are cyclooxygenase inhibitors. Pain relievers only alleviate OA syndromes but do not prevent the development of this disease; nonsteroidal anti-inflammatory drugs, on the other hand, have been found to exhibit various side effects, such as gastrointestinal toxicity and cardiovascular adverse effects. See Manathip et al., *Arthritis Care & Research* 1999, 12(5): 351-362; Hinz B et al, *Nat Clin Pract Rheumatol.* 2007 October; 3(10):552-60; quiz 1 p following 589. Thus, there is a need to develop new OA drugs.

BRIEF SUMMARY OF THE INVENTION

The present invention is based on the unexpected discovery that certain cycloartane compounds, obtained from *A. membranaceous*, inhibit the expression of matrix metalloproteinases 1 (MMP1), thereby effective in treating OA.

Accordingly, one aspect of the invention relates to a method of treating a disease associated with cartilage defect, e.g., OA, in a subject in need thereof by administering to the subject an effective amount of a cycloartane compound of Formula I:

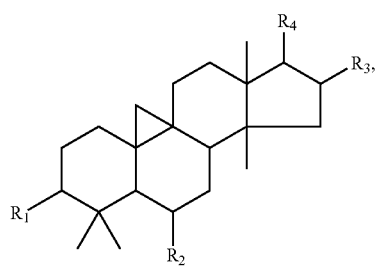

Formula I

In Formula I, $R_1$ is H, OH, O-acetyl, O-xylopyranosyl, O-(2-actetylxylopyranosyl), O-(3-actetylxylopyranosyl), O-(2,3-diactetylxylopyranosyl), O-(2,4-diactetylxylopyranosyl), O-(2,3,4-triactetylxylopyranosyl), O-xylopyranosyl-(1-2)-β-D-glucopyranosyl, or O-xylopyranosyl-(1-2)-α-D-arabinopyranosyl; $R_2$ is H, OH, O-acetyl, O-glucopyranosyl, or O-xylopyranosyl; $R_3$ is H, OH, or O-acetyl; and $R_4$ is

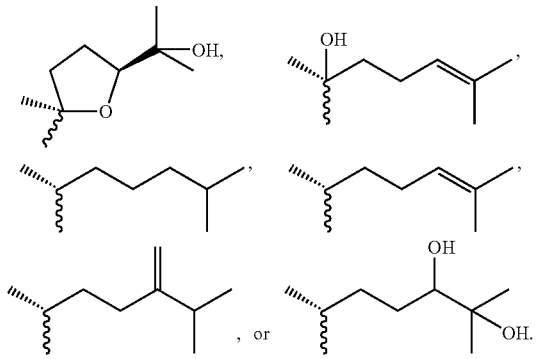

In an exemplary compound, $R_1$ is OH, $R_2$ is O-glucopyranosyl, $R_3$ is OH, and $R_4$ is

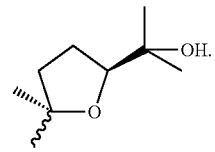

Formula II below encompasses more exemplary compounds:

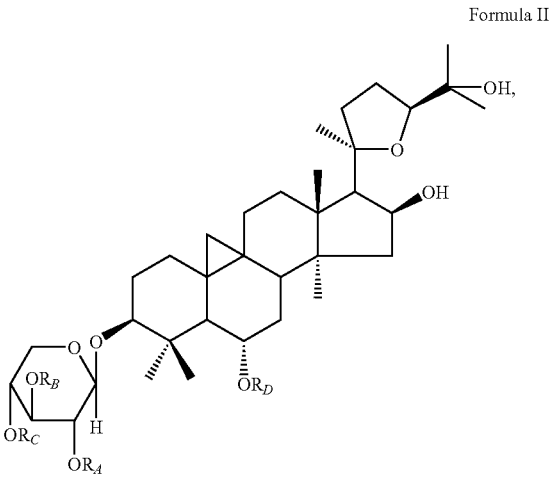

Formula II

In Formula II, $R_A$ is H, acetyl (Ac), or glucopyranoside (Glc); each of $R_B$ and $R_C$, independently, are Ac or H; and $R_D$ is H, Ac, or Glc.

Unless specified, acetyl, glucopyranoside, xylopyranosyl, actetylxylopyranosyl), arabinopyranosyl mentioned herein and the above-listed assignments of $R_4$ include both substituted and unsubstituted moieties. The term "substituted" denotes one or more substituents, which may be the same or different. Examples of substituents include, but are not limited to, halogen, cyano, nitro, hydroxyl, amino, mercapto, alkyl, alkenyl, alkynyl, aryl, heteroaryl, cyclyl, heterocyclyl, alkyloxy, aryloxy, alksulfanyl, arylsulfanyl, alkylamino, arylamino, dialkylamino, diarylamino, alkylcarbonyl, arylcarbonyl, heteroarylcarbonyl, alkylcarboxyl, arylcarboxyl, heteroarylcarboxyl, alkyloxycarbonyl, aryloxycarbonyl, heteroaryloxycarbonyl, alkylcarbamido, arylcarbamido, heterocarbamido, alkylcarbamyl, arylcarbamyl, heterocarbamyl, wherein alkyl, alkenyl, aryl, heteroaryl, cyclyl, or heterocyclyl in the above-listed substitutents, if any, is optionally substituted with halogen, cyano, nitro, hydroxyl, amino, mercapto, alkyl, aryl, heteroaryl, alkyloxy, aryloxy, alkylcarbonyl, arylcarbonyl, alkylcarboxyl, arylcarboxyl, alkyloxycarbonyl, or aryloxycarbonyl.

The term "treating" as used herein refers to the application or administration of a composition including one or more active agents to a subject, who has a disease associated with cartilage defect (e.g., OA), a symptom of the disease, or a predisposition toward the disease, with the purpose to cure, heal, alleviate, relieve, alter, remedy, ameliorate, improve, or affect the disease, the symptoms of disease, or the predisposition toward the disease. An "effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents. In one example, an effective amount of one of the cycloartane compounds described herein reduces MMP1 expression or inhibits cartilage loss in a subject in need of the treatment.

Also within the scope of this invention is use of the cycloartane compound of Formula (I) for treating cartilage defect-associated diseases, and for the manufacture of a medicament for these treatments.

The details of one or more embodiments of the invention are set forth in the description below. Other features or advantages of the present invention will be apparent from the following drawings and detailed description of several embodiments, and also from the appending claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1A:
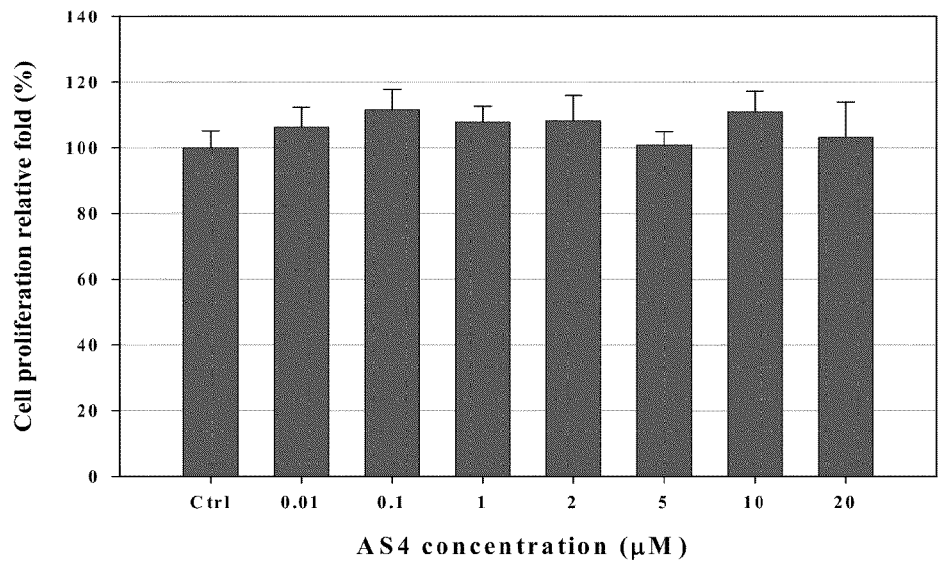
FIG. 1A is a histogram demonstrating the relative cell proliferation folds with different AS4 concentrations after 24 hours of incubation. * indicates $p<0.05$; ** indicates $p<0.01$; and "Ctrl" refers to the control group.

As used herein the following terms may be used for better interpretation of the claims and specification.

The articles "a" and "an" are used herein to refer to one or more than one (i.e., at least one) of the grammatical object of the article. By way of example, "an element" means one element or more than one element.

The present invention relates to a method of treating a cartilage defect-associated disease, e.g., OA, by administering to a subject in need of the treatment an effective amount of a cycloartane compound of Formula (I) described above.

Set forth below are exemplary cycloartane compounds for use in the method of this invention. These exemplary compounds have Formula (II):

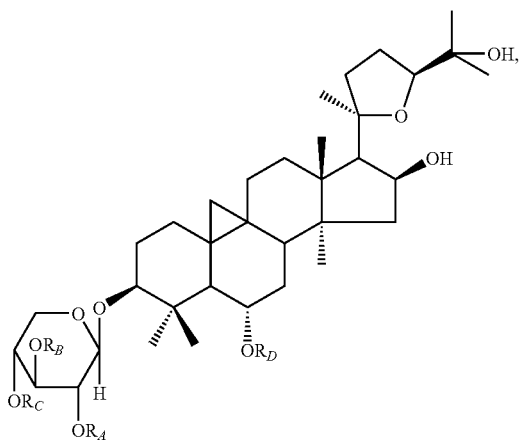

Formula (II)
in which the moieties of $R_A$, $R_B$, $R_C$, and $R_D$ are:

| Compound Name | $R_A$ | $R_B$ | $R_C$ | $R_D$ |
|---|---|---|---|---|
| Astragaloside I, (AS1) | Ac | Ac | H | Glc |
| Astragaloside II (AS2) | Ac | H | H | Glc |
| Astragaloside III (AS3) | Glc | H | H | H |
| Astragaloside IV (AS4) | H | H | H | Glc |
| Astragaloside VI (AS6) | Glc | H | H | Glc |
| Isoastragaloside I (IsoAS1) | Ac | H | Ac | Glc |
| Isoastragaloside II (IsoAS2) | H | Ac | H | Glc |

Any of the cycloartane compounds described above can be prepared by chemical synthesis or isolation from a natural source, e.g., *A. membranaceous*. In one example, the cycloartane compound is a component of an alcoholic extract of *A. membranaceous*. The term "alcoholic *A. membranaceous* extract" used herein refers to an extract prepared by extracting *A. membranaceous* (e.g., rhizome of the plant) with an alcohol (e.g., methanol or ethanol) or a solvent containing an alcohol, e.g., a solvent containing ethanol or methanol at a concentration of 10% or higher (v/v). The cycloartane compound-containing *A. membranaceous* extract can be prepared as follows. Roots of *A. membranaceous* are dried and soaked in ethanol at a suitable temperature (e.g., 20-70° C.) for a sufficient period of time (e.g., 1 to 72 hours) and insoluble substances are removed by, e.g., filtration, to produce an ethanolic extract of *A. membranaceous* in liquid form. Optionally, the *A. membranaceous* ethanolic extract is further mixed with water and the water-insoluble fraction is then collected to obtain another *A. membranaceous* extract that contains one or more of the cyclortane compounds used in this invention.

In one example, the cycloartane compounds described herein are prepared as follows. Dried rhizome of *A. membranaceous* was extracted with 95% ethanol (50 L×5) at room temperature. The extract thus obtained was concentrated under reduced pressure to yield a brown syrupy mass. This syrupy mass was dissolved in water and then partitioned (1:1) with n-butanol to obtain an n-butanol soluble fraction and a water soluble fraction. The n-butanol soluble fraction was subjected to medium-pressure liquid chromatography (MPLC) ($C_8$ column; 70% MeOH/$H_2O$) to generate three fractions. Among them, the second fraction was subjected to further column chromatography over a silica gel (70-230 mesh) using $CHCl_3$—MeOH—$H_2O$ (10:5:1) step gradient as eluents and Astragaloside I, Astragaloside II, Astragaloside III, Astragaloside IV, Astragaloside VI, Isoastragaloside I, and Isoastragaloside II, contained in different fractions, were obtained. If desired, Astragaloside IV can be hydrolyzed using naringinase to produce additional cycloartane compounds, such as cycloastragenol 6-O-β-D-glucopyranose (hereinafter as AA), an astragaloside of formula (I), wherein $R_1$ is OH, $R_2$ is O-glucopyranosyl, $R_3$ is OH, and $R_4$ is:

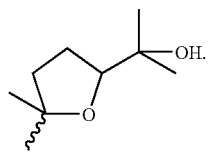

See Kitagawa et al., *Chem. Pharm. Bull.*, 1983, 31(2): 689-697; Kitagawa et al., *Chem. Pharm. Bull.*, 1983, 31(2): 698-708; See Kitagawa et al., *Chem. Pharm. Bull.*, 1983, 31(2): 709-715.

The cycloartane compound described above can be used to treat osteroarthritis or a joint disease/disorder associated with cartilage defect. As used herein, the term "cartilage defect" refers to the situation where the cartilage in a certain joint area is defective or is at risk for developing defects. Various conditions can cause cartilage defect, including trauma, osteonecrosis, osteochondritis, aging, and arthritis.

Without being bound by theory, the cycloartane compounds described herein may function through inhibiting the expression of matrix metalloproteinases (MMPs) and increasing the expression of tissue inhibitors of metalloproteases (TIMPs), which are specific inhibitors of MMPs. As shown in Examples 2-7 below, several exemplary cycloartane compounds described herein inhibit MMP expression and activate TIMP expression, thereby protecting collagen, thus cartilage, from degradation.

To use any of the cyclortane compounds described herein for treating osteroarthritis or joint disease/disorder associated with cartilage defect, the compound can be formulated as a pharmaceutical composition and administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

In one embodiment, the cycloartane compound is delivered by intra-articular administration. As used herein, "intra-articular administration" refers to direct injection of the extract of *Astragalus membranaceous* into the joint area in a subject in need. A skilled person in the art would know how to select a buffer for injection, and the volume and the effective amount may easily be determined according to his knowledge and standard methodology of merely routine experimentation based on the present disclosure. Moreover, a skilled person in the art can mix any well known active agent with the cycloartane compound for injection to improve the therapeutic effect.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. An cycloartane compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the cycloartane compounds, or one or more solubilizing agents, can be utilized as pharmaceutical excipients for delivery of the cycloartane compounds. Examples of other carriers include colloidal silicon dioxide, magnesium stearate, cellulose, sodium lauryl sulfate, and D&C Yellow #10.

The cycloartane compounds can be preliminarily screened for their efficacy in the desired treatments by one or more of the assays described in the Examples below.

The cycloartane compounds described herein can be a component of a food product or a food supplement (e.g., a nutrient supply or an herbal product). Such food products may be prepared with an alcoholic extract of *A. membranaceous* extract by any standard or commonly used methods in the food industry.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Effects of Astragaloside IV on Cell Viability in Human SW1353 Cell Line

SW1353 Cell Culture

The spontaneously transformed human chondrosarcoma cell line SW1353 was grown at 37° C. in a humidified incubator under 5% $CO_2$ and 95% air in culture medium such as Dulbecco Modified Eagle Medium (DMEM) supplemented with 10% Fetal Bovine Serum (FBS). The culture medium was replaced every other day. After confluence, the cells were subcultured following trypsinization. For subcultures, cells were harvested after brief treatment with 0.1% trypsin/ethylenediaminetetraacetic acid (EDTA) solution and seeded at a dilution of 1:10. Cells between passages 12 and 45 were used for studies.

In the control group, SW1353 cells were maintained in medium supplemented with the vehicle (dimethyl sulfoxide (DMSO) 0.1%). No growth and differentiation effects of DMSO were observed under these culture conditions. In experimental groups, SW1353 cells were first cultured in the said medium for 24 hours and then sub-cultured in serum free medium for another 24 hours. Then, SW1353 cells were treated with 100 ng/mL PMA or 10 ng/mL IL-1β, followed by incubating for 24 hours in order to induce inflammation reaction, and these SW1353 cells were ready for the following drug testing.

Cell Viability Assay

The SW1353 cells were sub-cultured in 96-well culture plates at an average amount of 5,000 cells per well and incubated at 37° C. in a humidified incubator with 5% $CO_2$ for 24 hours. Then SW1353 cells were treated with astragaloside IV (AS4) at a concentration of 0.01 μM, 0.1 μM, 1 μM, 2 μM, 5 μM, 10 μM or 20 μM, followed by incubating for 24 hours or 48 hours. Later, the SW1353 cell culture in each well was treated with 10 μl Cell Counting Kit 8 solution (Dojindo molecular technologies, Gaithersburg, Md., USA), followed by incubation at 37° C. in a humidified incubator with 5% $CO_2$ for 1-4 hours. Then, the absorbance of the SW1353 cell cultures was detected by an EIA reader at 450 nm. Compared with that of the control group, the viability of the experimental groups was analyzed.

Figure 1B:
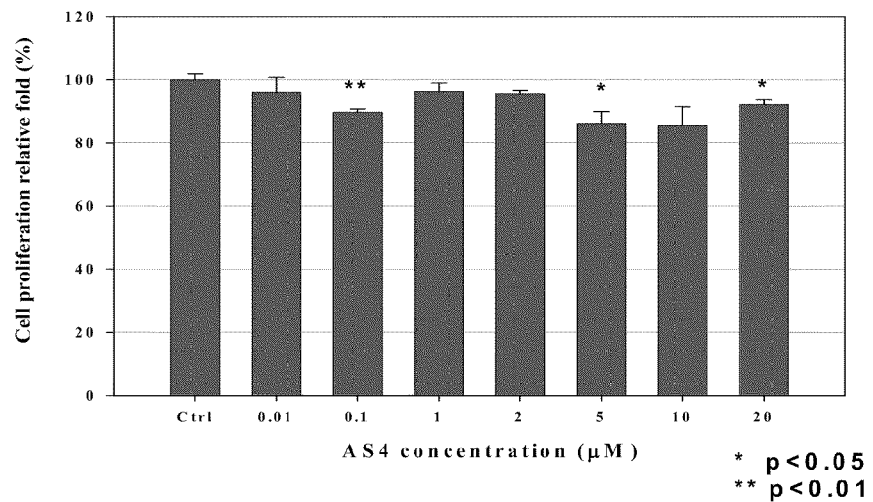
FIG. 1B is a histogram demonstrating the relative cell proliferation folds with different AS4 concentrations after 48 hours of incubation. * indicates $p<0.05$; ** indicates $p<0.01$; and "Ctrl" refers to the control group.

Referring to FIG. 1A, after being treated with astragaloside IV (AS4) for 24 hours, the cell proliferation of the experimental groups did not change significantly compared with that of the control group. Referring to FIG. 1B, after being treated with astragaloside IV (AS4) for 48 hours, the cell proliferation of the experimental groups did not change significantly compared with that of control group, either. These results suggest that astragaloside IV (AS4) is non-toxic to SW1353 cells.

EXAMPLE 2

Effects of Astragaloside IV on MMP1 Expression Induced by PMA in Human SW1353 Cell Line The SW1353 cells were grown at 37° C. in a humidified incubator under 5% $CO_2$ and 95% air in the culture medium stated as above. The SW1353 cells were then sub-cultured into 6 wells culture plate with serum free medium at an average amount of $2 \times 10^5$ cells per well, followed by incubation for 24 hours. Then the SW1353 cells were treated with astragaloside IV (AS4) at a concentration of 0.0001 μM, 0.0005 μM, 0.001 μM, 0.005 μM, 0.01 μM, 0.1 μM or 1 μM, followed by incubation for 24 hours. Alternatively, the control group was treated with 0.1% dimethyl sulfoxide (DMSO). Phorbol myristate acetate (PMA; Sigma, St. Louis, Mo.) at a concentration of 100 ng/mL was then added into each well and the cells were incubated for 24 hours. The culture medium was collected for western blotting analysis.

Western Blotting Analysis

Western blotting analysis was carried out based on the following procedure. Cells were washed and lysed in 0.2 mL of lysis buffer (1% NP-40, 50 mM Tris-HCl, pH 7.4, 180 mM NaCl, 1 mM EDTA, 1 mM PMSF, 1 mM NaF, 10 mM $Na_3VO_4$) for 30 min at 4° C. After centrifugation at 17500 g for 15 min, the supernatants of cell lysate were collected. Protein concentrations of the samples were measured using the bicinchoninic acid (BCA) protein assay kit according to the manufacturer's protocol (Pierce, Rockford, Ill., USA). Equal amounts of protein samples of concentrated conditioned medium (100 μg) or cell lysate supernatants (50 μg) were mixed with an appropriate volume of 4×SDS sampling buffer and separated on a 8% SDS-PAGE gel. The protein bands separated on the SDS-PAGE gel were blotted onto a polyvinylidene fluoride (PVDF) membrane. The blotted PVDF membrane was washed twice and blocked in freshly prepared Tris-buffered saline (TBS) containing 0.1% Tween-20 and 7% skim milk (TBST) for 2 hours at room temperature. The PVDF membrane was then incubated with a primary antibody against MMP1 protein (Santa Cruz Biotechnology, Santa Cruz, Calif.) for 18 hours at 4° C. Horseradish peroxidase-conjugated anti-goat antibody was used as the secondary antibody. Signals were visualized by an enhanced chemiluminescence kit (Clonetech, Palo Alto, Calif., USA) followed by exposure to X-ray films.

Figure 2A:
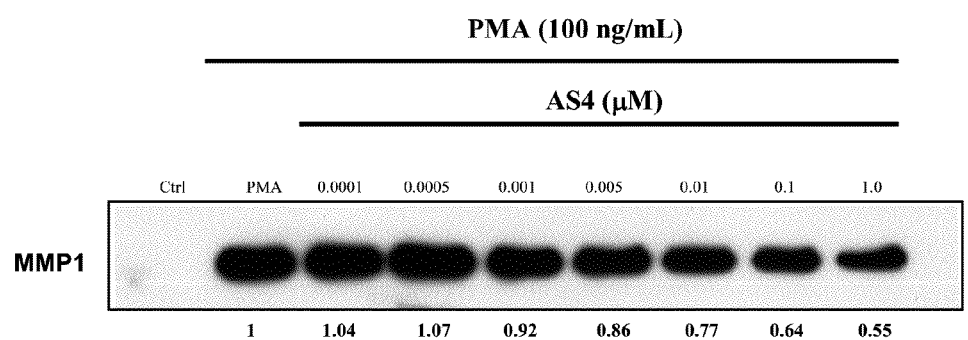
FIG. 2A is the result of western blotting analysis demonstrating the effect of different concentrations of AS4 on MMP1 protein expression induced by PMA. "Ctrl" refers to the control group.

Referring to FIG. 2A, the level of MMP1 protein expression of the group without AS4 treatment was set as 1. After treatment with AS4 at the concentrations of 0.01 μM, 0.1 μM, and 1 μM, the level of MMP1 protein expression was decreased by 0.77, 0.64 and 0.55, respectively. As a result, it was found that after incubation with AS4, the MMP1 protein expression was decreased.

In another testing, the SW1353 cells were treated with 0.1 μM astragaloside IV (AS4), followed by incubation for 24 hours. PMA at a concentration of 100 ng/mL was then added into each well. The culture medium was collected after 6, 12, 18 and 24 hours of PMA treatment for western blotting analysis.

Figure 2B:
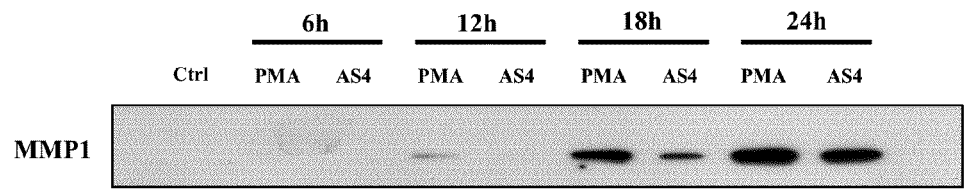
FIG. 2B is the result of western blotting analysis demonstrating the effect of AS4 on MMP1 protein expression induced by PMA at different time points. "Ctrl" refers to the control group.

Referring to FIG. 2B, the level of expression of MMP1 protein was inhibited after AS4 treatment at different time points, compared with that after only PMA treatment. Therefore, this result indicated that AS4 reduced the inflammation reaction induced by PMA.

EXAMPLE 3

Effects of Astragaloside IV on MMP1 Expression Induced by Different Inducers in Human SW1353 Cell Line Based on the same protocol described in Example 2, the SW1353 cells were grown at 37° C. in a humidified incubator under 5% $CO_2$ and 95% air in the culture medium as above. The SW1353 cells were then sub-cultured into 6-well culture plates with serum free medium at an average amount of 2×10$^5$ cells per well, followed by incubation for 24 hours. Then the SW1353 cells were treated with astragaloside IV (AS4) at a concentration of 0.01 μM, 0.1 μM, or 1 μM, followed by incubation for 24 hours. Alternatively, the control group was treated with 0.2% dimethyl sulfoxide (DMSO). In the experimental groups, 100 ng/mL PMA, 10 ng/mL IL-1β, and 10 ng/mL TNF-α were then added into each well and the cells were further incubated for 24 hours. The cell cultures finally were collected for western blotting analysis as described in Example 2.

Figure 3:
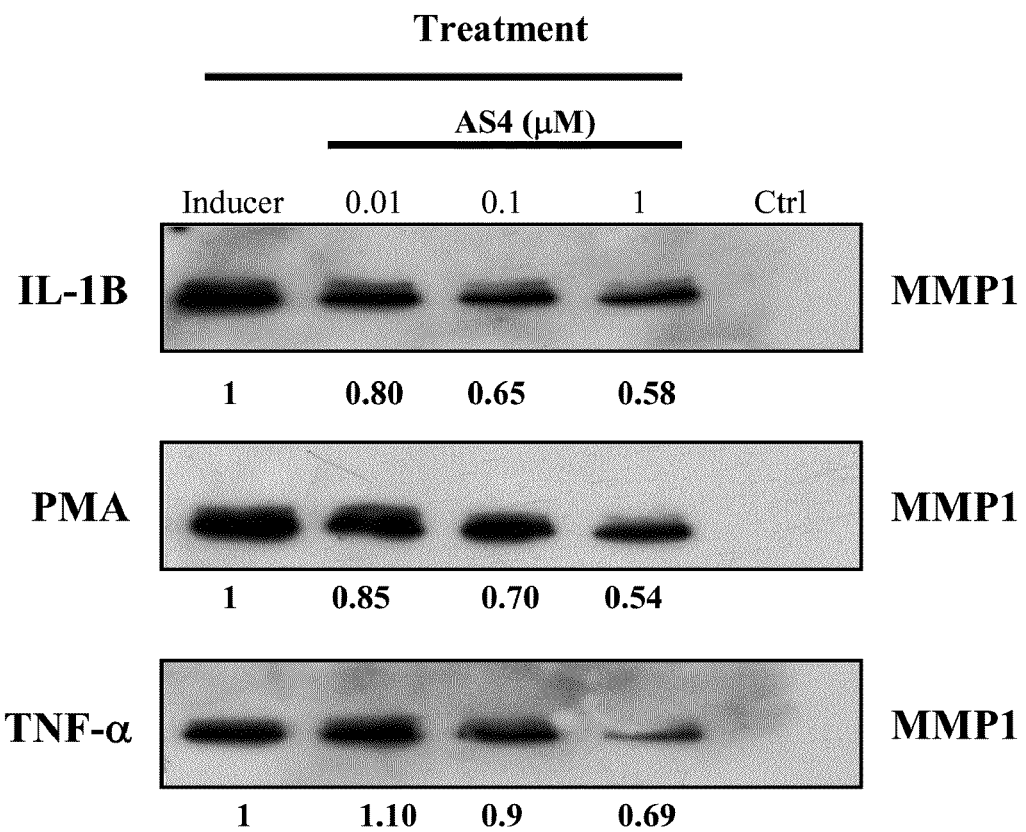
FIG. 3 is the result of western blotting analysis demonstrating the effect of AS4 on MMP1 protein expression induced by IL-1β, PMA, and TNF-α after 24 hours of treatment. "Ctrl" refers to the control group

Referring to FIG. 3, the level of expression of MMP1 protein was inhibited after AS4 treatment even though the cell cultures were treated with different inducers, compared with the cell culture treated with only PMA. Therefore, this result suggested that AS4 treatment can reduce the MMP1 protein expression induced by different inducers such as IL-1β, PMA or TNF-α.

EXAMPLE 4

Effects of Astragaloside IV on MMP1 mRNA Expression and TIMP1 mRNA Expression Induced by PMA in Human SW1353 Cell Line First of all, the interaction between TIMP1 mRNA expression and MMP1 mRNA expression in human SW1353 cell line after only AS4 treatment was studied. The SW1353 cells were first grown at 37° C. in a humidified incubator under 5% $CO_2$ and 95% air in the culture medium as above. The SW1353 cells were then sub-cultured into 6-well culture plates with serum free medium at an average amount of 2×10$^5$ cells per well, followed by incubation for 24 hours. Then the SW1353 cells were treated with astragaloside IV (AS4) at the concentrations of 0.01 μM, 0.1 μM, and 1 μM, followed by incubation for 24 hours. The SW1353 cells were then collected for RT-PCR analysis.

In a second testing, the effect of AS4 treatment followed by PMA treatment was also studied. The SW1353 cells were first treated with astragaloside IV (AS4) at a concentration of 0.01 μM, 0.1 μM, or 1 μM, followed by incubation for 24 hours. Then PMA was added into each well, followed by incubation for 24 hours. These SW1353 cells were also collected for RT-PCR analysis in the end of the second testing.

Total RNAs were isolated from the cultured human cells using NucleoSpin RNAII Kit (Macherey-Nagel Inc., PA, USA). Five μg of RNA was reverse transcribed in a total 20 μl transcription mixture. The reaction tube containing primers (oligo(dT)), RNA, 10 mM dNTP Mix, and DEPC-treated water was first incubated at 65° C. for 5 minutes. Eight μl master reaction mixture containing 4 μl 5× cDNA synthesis Buffer, 1 μl 0.1 M DTT, 1 μl RNase OUT™ (40U/μl), 1 μl DEPC-Treated water, and 1 μl SuperScript™II was then added into the reaction tube. The reaction tube was then incubated at 50° C. for 60 minutes, followed by incubation at 85° C. for 5 minutes. Finally, 1 μl RNase H was added at 37° C. and the reaction tube was incubated for 20 minutes. The resulting cDNA was further amplified by PCR. The relevant primers for the following PCR reaction were listed below.

(i) The MMP1 forward primer is 5'-ACT CTG GAG TAA TGT CAC ACC T-3' (SEQ ID NO: 1), and the MMP1 reverse primer is 5'-GTT GGT CCA CCT TTC ATC TTC A-3' (SEQ ID NO: 2);

(ii) the TIMP1 forward primer is 5'-AAT TCC GAC CTC GTC ATC AG-3' (SEQ ID NO: 3) and the TIMP1 reverse primer is 5'-TGC AGT TTT CCA GCA ATG AG-3' (SEQ ID NO: 4); and (iii) the GAPDH forward primer is 5'-TGG TAT CGT GGA AGG ACT CA-3' (SEQ ID NO: 5) and the GAPDH reverse primer is 5'-AGT GGG TGT CGC TGT TAT AAA GC-3' (SEQ ID NO: 6).

In addition, the PCR reaction of MMP1 cDNA was preformed as follows: 95° C. for 5 min, followed by 35 cycles of 94° C. for 30 sec, 60° C. for 30 sec, and 72° C. for 30 sec, and then 72° C. for 10 min followed by maintaining at 4° C. Similarly, the PCR reaction of TIMP1 cDNA was performed as follows: 94° C. for 5 min, followed by 35 cycles of 94° C. for 30 sec, 60° C. for 30 sec, and 72° C. for 30 sec, and then 72° C. for 10 min followed by maintaining at 4° C. The PCR reaction of GAPDH cDNA was performed as follows: 94° C. for 5 min, followed by 18 cycles of 94° C. for 30 sec, 54° C. for 30 sec, and 72° C. for 30 sec, and then 72° C. for 30 sec followed by maintaining at 4° C. These PCR products were analyzed by electrophoresis on a 1.5% gel.

Figure 4A:
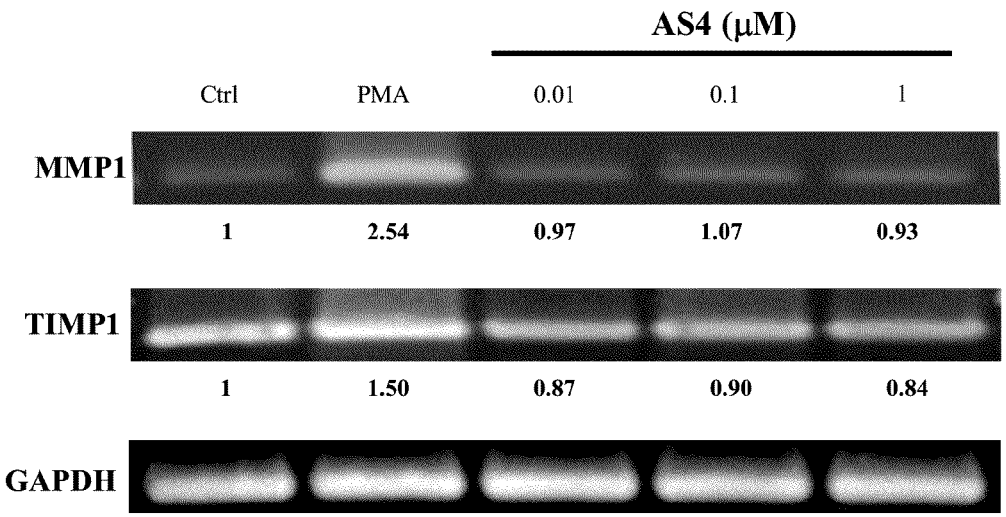
FIG. 4A is the result of PCR analysis demonstrating the effect of AS4 on non-induced MMP1 and TIMP1 mRNA expression. "Ctrl" refers to the control group.

Referring to FIG. 4A, the level of mRNA expression of MMP1 and TIMP1 in human SW1353 cells after only AS4 treatment was shown. The values of MMP1 expression after only AS4 treatment at the concentrations of 0.01 μM, 0.1 μM and 1 μM were 0.97, 1.07 and 0.93, respectively, and the values of TIMP expression after only AS4 treatment at the concentrations of 0.01 μM, 0.1 μM and 1 μM were 0.87, 0.90 and 0.84, respectively. As a result, it was found that treatment with only AS4, that is, without PMA, does not inhibit MMP1 expression.

Figure 4B:
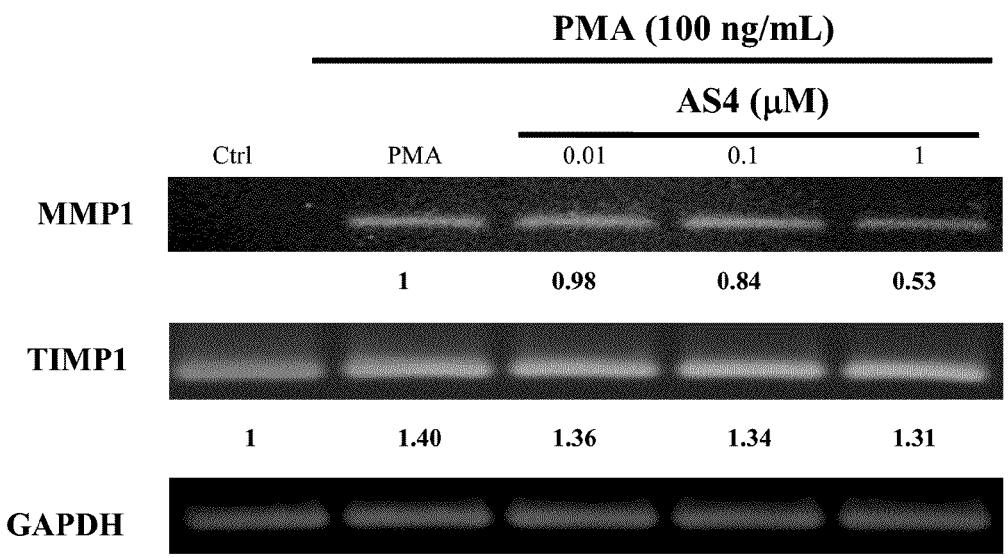
FIG. 4B is the result of PCR analysis demonstrating the effect of AS4 on MMP1 and TIMP1 mRNA expression induced by PMA. "Ctrl" refers to the control group.

Referring to FIG. 4B, the level of mRNA expression of MMP1 and TIMP1 in human SW1353 cells after AS4 treatment followed by PMA treatment was shown. The values of MMP1 expression after AS4 treatment at the concentrations of 0.01 μM, 0.1 μM and 1 μM, followed by treating with 100 ng/mL PMA, were 0.98, 0.84 and 0.53, respectively. The values of TIMP1 expression after AS4 treatment at the concentrations of 0.01 μM, 0.1 μM and 1 μM, followed by treating with 100 ng/mL PMA, were 1.36, 1.34 and 1.31, respectively. As a result, it was found that the AS4 treatment decreased MMP1 expression induced by PMA, suggesting that AS4 can inhibit inflammation induced by PMA treatment.

EXAMPLE 5

Effects of Astragaloside IV on Signal Transduction Pathway of MMP1 Protein Expression Induced by PMA in Human SW1353 Cell Line The SW1353 cells were grown at 37° C. in a humidified incubator under 5% $CO_2$ and 95% air in the culture medium as described above. The SW1353 cells were then sub-cultured into 6-well culture plates with serum free medium at an average amount of $2 \times 10^5$ cells per well and incubated for 24 hours. Then, the SW1353 cells were treated with 10 μM UO126 (MEK1-specific inhibitor), 25 μM, SP600125 (JNK-specific inhibitor), 5 μM SB203580 (p38-specific inhibitor), or 20 μM LY294002 (PI3K kinase inhibitor), and incubated for another 24 hours. Later, the SW1353 cells were treated with 100 ng/mL PMA and again incubated for 24 hours. Finally, the SW1353 cells were under cell extraction and the cell lysate was used for further luciferase analysis and western blotting analysis.

Luciferase Analysis

The SW1353 cells were grown at 37° C. in a humidified incubator under 5% $CO_2$ and 95% air in the culture medium as described above. The SW1353 cells were then sub-cultured into 24-well culture plates and cultured for 24 hours. One μg DNA was mixed with 25 μl 150 mM NaCl in tube 1, while 1 μg jetPEI™ (Cationic Polymer Transfection, USA) was mixed with 25 μl 150 mM NaCl in tube 2. Solution in tube 2 was transferred to tube 1 and then the mixture was incubated for 15-30 minutes under room temperature. Then 50 μl the mixture was transferred to each well of a cell culture plate and incubated at 37° C. in a humidified incubator under 5% $CO_2$ overnight. Following cell extraction, the cell lysate was centrifuged at 4° C., 20000 g for 30 minutes and then transferred to a 1.5 ml-microcentrifuge tube. Then, 100 μl buffer A (0.1 mM luciferin) and 350 μl buffer B (1 M $MgSO_4$, 1 M Hepes (pH 7.8), 0.1 M ATP) were added into the microcentrifuge tube. The luciferase activity of final mixture was measured by a luminometer for 30 seconds.

Figure 5A:
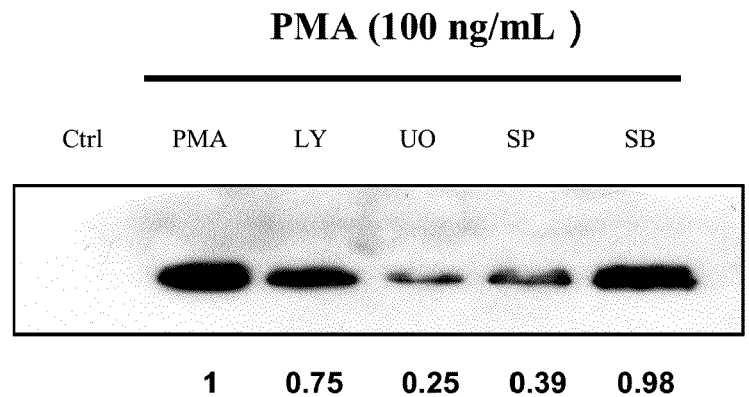
FIG. 5A is the result of western blotting analysis demonstrating the effect of PI3K kinase inhibitor (LY), MEK1-specific inhibitor (UO), JNK-specific inhibitor (SP), and p38-specific inhibitor (SB) on MMP1 protein expression induced by PMA. "Ctrl" refers to the control group.

Referring to FIG. 5A, based on the result of western blotting, the MEK1 (UO) and JNK (SP) protein expressions were significantly reduced, suggesting that MEK1 and JNK are involved in the MMP1 expression pathway induced by PMA.

Figure 5B:
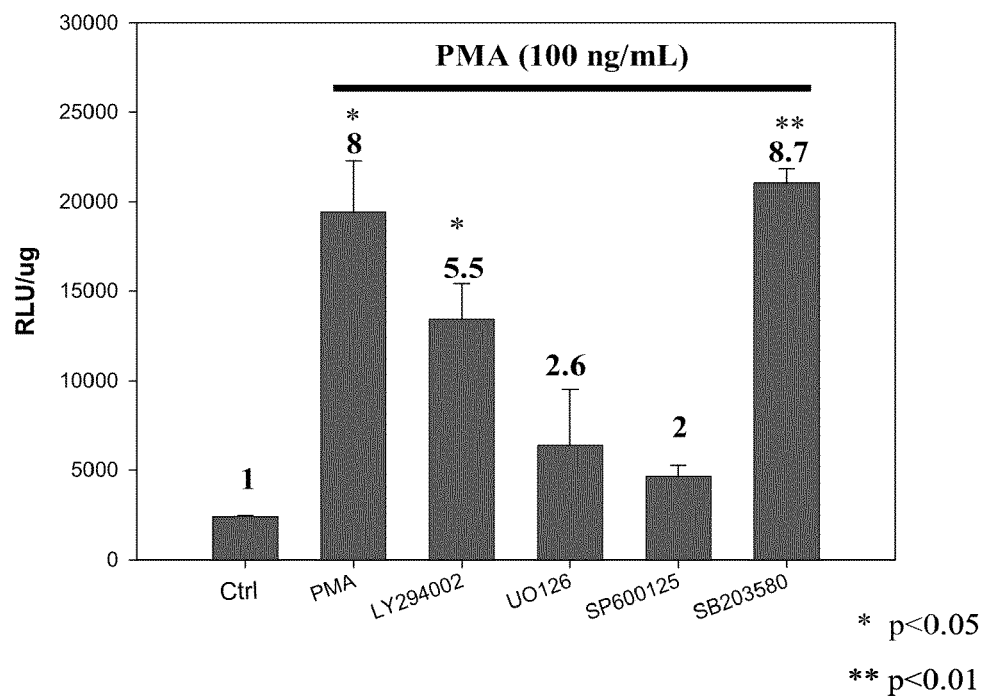
FIG. 5B is a histogram demonstrating the effect of PI3K kinase inhibitor (LY), MEK1-specific inhibitor (UO), JNK-specific inhibitor (SP), and p38-specific inhibitor (SB) on MMP1 protein expression induced by PMA, analyzed by luciferase analysis. * indicates $P<0.05$; ** indicates $P<0.01$; and "Ctrl" refers to the control group.

Referring to FIG. 5B, based on the result of luciferase activity assay, the MEK1 expression (UO126) was reduced by 2.6 fold and the JNK expression (SB203580) was reduced by 2 fold, compared with the control group (1 fold) and PMA-only group (8 fold), also suggesting that MEK1 and JNK are involved in the MMP1 expression pathway induced by PMA.

In another experiment, the SW1353 cells were grown at 37° C. in a humidified incubator under 5% $CO_2$ and 95% air in the culture medium as described above. The SW1353 cells were then sub-cultured into 24-well culture plates with serum free medium at an average amount of $5 \times 10^4$ cells per well and incubated for 24 hours. The SW1353 cells were treated with 100 ng/mL PMA and incubated for 2 hours. Then, the SW1353 cells were treated with 1 μM AS4 and cultured for another 24 hours, followed by cell extraction and western blotting analysis.

Figure 5C:
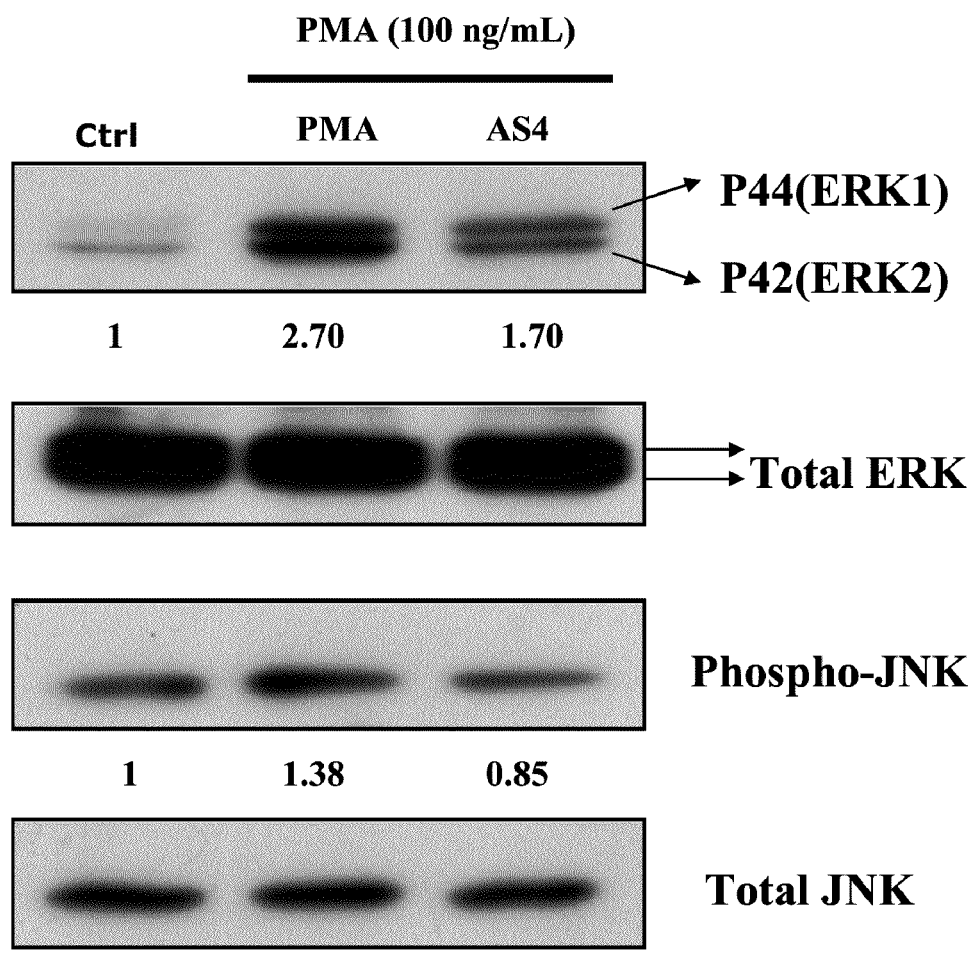
FIG. 5C is the result of western blotting analysis demonstrating the effect of AS4 on the signal transduction pathway of MMP1 protein expression induced by PMA. "Ctrl" refers to the control group.

Referring to FIG. 5C, based on the results of western blotting, the value of expression of ERK1 (P44) and ERK2 (P42) was decreased from 2.7 to 1.7, suggesting that ERKs are involved in the MMP1 expression pathway induced by PMA. The control group was treated with 0.1% DMSO.

EXAMPLE 6

Effects of Other Astragaloside Compounds on MMP Expression Induced by PMA or IL-1β in Human SW1353 Cell Line Western Blotting Analysis The SW1353 cells were grown at 37° C. in a humidified incubator under 5% $CO_2$ and 95% air in the culture medium as described above. The cells were then plated on 6-cm dishes at a density of $1 \times 10^6$ cells/dish for 24 hours prior to any treatment. At the beginning of the experiment, the cells were pre-treated with 100 ng/mL PMA or 10 ng/mL IL-1β for 24 hours. The cells were then treated 0.1 μM Dexamethasone with, various astragaloside compounds (0.1 μM) or extracts of *Astragalus membranaceous* (1 μg/mL) at indicated dosages for another 48 hours. For control sample, 0.1% DMSO was used as a negative control for these experiments. The conditioned culture mediums were then centrifuged, 2-fold concentrated and collected for assay of collagens or MMPs secreted into the culture medium.

Western blotting analysis was carried out on both cultured medium and cell lysates, as follows. The cells were washed and lysed in 0.2 mL of lysis buffer (1% NP-40, 50 mM Tris-HCl, pH 7.4, 180 mM NaCl, 1 mM EDTA, 1 mM PMSF, 1 mM NaF, 10 mM $Na_3VO_4$) for 30 min at 4° C. After centrifuging at 17500 g for 15 min, the supernatants of cell lysate were also collected. Protein concentration of the samples were measured using the bicinchoninic acid (BCA) protein assay kit according to the manufacturer's protocol (Pierce, Rockford, Ill., USA). Equal amount of protein samples of concentrated conditioned medium (100 μg) or cell lysate supernatants (50 μg) were mixed with an appropriate volume of 4×SDS sampling buffer and separated by 8% SDS- PAGE gel. The protein bands separated in the SDS-PAGE gel were blotted onto a polyvinylidene fluoride (PVDF) membrane. The blotted PVDF membrane was washed twice and blocked in freshly prepared Tris-buffered saline (TBS) containing 0.1% Tween-20 and 7% skim milk (TBST) for 2 hours at room temperature. The PVDF membrane was then incubated with either antibodies against collagen I and III or the housekeeping protein α-tubulin (Santa Cruz Biotechnology, Santa Cruz, Calif.) for 18 hours at 4° C. Horseradish peroxidase-conjugated anti-goat antibody was used as secondary antibody. Signals were visualized by an enhanced chemiluminescence kit (Clonetech, Palo Alto, Calif., USA) followed by exposure to X-ray films.

As shown in the following Tables 1-4, the MMP expression induced by PMA or IL-1β in human SW1353 cells was inhibited by the astragaloside compounds of the present invention, so that both cytoplasmic and secreted MMP levels were reduced. These results indicate that the tissue damage by inflammation due to the release of MMPs can be reduced by the astragaloside compounds of the present invention.

TABLE 1

Western blot results (PMA-pre-treated SW1353 cell extract)

|        | Ctrl | Dex  | AS1  | AS2  | AS4  | IsoAS1 | IsoAS2 |
|--------|------|------|------|------|------|--------|--------|
| MMP-1  | 1.00 | 0.38 | 0.86 | 0.71 | 0.74 | 0.67   | 1.28   |
| MMP-13 | 1.00 | 0.48 | —    | —    | 0.79 | 1.19   | 0.60   |

TABLE 2

Western blot results (PMA-pre-treated SW1353 culture medium)

|        | Ctrl | Dex  | AS1  | AS6  | AA   | IsoAS1 | IsoAS2 |
|--------|------|------|------|------|------|--------|--------|
| MMP-1  | 1.00 | 0.60 | 0.48 | 0.40 | 0.52 | 0.77   | 0.77   |
| MMP-13 | 1.00 | 0.46 | 1.15 | 0.93 | 0.84 | 1.03   | 0.80   |

TABLE 3

Western blot results (IL-1β-pre-treated SW1353 cell extract)

|        | Ctrl | Dex  | AS1  | AS2  | AS3  | AS4  | AS6  | AA   | AS water insoluble fraction | AS ethanol fraction |
|--------|------|------|------|------|------|------|------|------|------|------|
| MMP-1  | 1.00 | 0.26 | 0.66 | 0.86 | 0.39 | 0.22 | 0.63 | 0.74 | 0.50 | 0.51 |
| MMP-13 | 1.00 | 0.64 | 0.37 | 0.49 | 0.86 | 1.10 | —    | —    | —    | —    |

TABLE 4

Western blot results (IL-1β-pre-treated SW1353 culture medium)

|        | Ctrl | Dex  | AS2  | AS3  | AS4  | AA   |
|--------|------|------|------|------|------|------|
| MMP-1  | 1.00 | 0.38 | —    | 0.09 | —    | 0.76 |
| MMP-13 | 1.00 | 0.29 | 0.45 | —    | 0.56 | 0.93 |

Zymography

The SW1353 cells were grown at 37° C. in a humidified incubator under 5% CO$_2$ and 95% air in the culture medium as described above. At the beginning of the experiment, the cells were pre-treated with 100 ng/mL PMA or 10 ng/mL IL-1β for 24 hours. The cells were then treated with 0.1 μM Dexamethasone, various astragaloside compounds (0.1 μM) or extracts of *Astragalus membranaceous* (1 μg/mL) at indicated dosages for another 24 hours. For control sample, 0.1% DMSO was used as a negative control for these experiments. The conditioned culture mediums were then centrifuged, 2-fold concentrated and collected for assay of collagens or MMPs secreted into the culture medium.

The proteolytic activities of MMPs from SW1353 cells were measured essentially as described previously (*Circ Res*, 1999; 85:906-911). The cells were lysed in lysis buffer (1% Triton X-100, 50 mM Tris-Cl, pH 7.4, 180 mM NaCl, 1 mM EDTA). The samples were measured for their protein concentration using the bicinchoninic acid (BCA) protein assay kit as described. Samples of concentrated conditioned medium and cell lysates were mixed with non-reducing electrophoresis loading buffer and subjected to electrophoresis under non-reducing conditions. The electrophoresis was carried out on a 10% SDS-PAGE co-polymerized with 2 mg/mL gelatin or casein (Sigma, St. Louis, Mo. USA). For zymographic analysis of pro-MMP-2 and activated MMP-2, the total 20 μg of culture medium were used for electrophoresis. Following electrophoresis, renaturation of the proteins was achieved by incubating the gels twice in 25 g/L Triton X-100 at room temperature for 10 min. Subsequently the gels were incubated in 50 mM Tris-HCl, pH 7.5 containing 0.2 M NaCl, 0.02% Brij35 and 10 mM CaCl$_2$ at 37° C. for 18 hours. After the gels were stained with Coomassie Brilliant Blue R-250 and destained, zones of proteolytic activities became visible as transparent bands in the stained gel. In order to obtain higher sensitivity, the gels were further destained in a solution of 1% Triton X-100 (1 to 2 hours). This procedure increased the signal-to-noise ratio, allowing the visualization of faint gelatinase bands at 92 kDa, 125 kDa and greater than 200 kDa. Zymograms were read using a Molecular Dynamics (Sunnyvale, Calif., USA) computing laser densitometer with Image Quant software.

As shown in the following Tables 5 and 6, the activities of MMPs induced by PMA or IL-1β in human SW1353 cells were inhibited by the astragaloside compounds of the present invention. These results indicate that the tissue damage by inflammation can be reduced by the astragaloside compounds of the present invention.

TABLE 5

Zymography results (PMA-pre-treated SW1353)

|       | Ctrl | Dex  | AS1  | AS3  | AS4  | IsoAS1 | IsoAS2 |
|-------|------|------|------|------|------|--------|--------|
| MMP-1 | 1.00 | 0.87 | 0.85 | 0.89 | 0.68 | 0.66   | 0.95   |
| MMP-2 | 1.00 | 0.99 | 0.87 | 0.90 | 1.01 | 1.01   | 1.04   |
| MMP-9 | 1.00 | 0.92 | 1.23 | 0.87 | 1.04 | 0.85   | 0.95   |

TABLE 6

Zymography results (IL-1β-pre-treated SW1353)

| | Ctrl | Dex | AS1 | AS2 | AS water insoluble fraction | AS ethanol fraction |
|---|---|---|---|---|---|---|
| MMP-1 | 1.00 | 0.80 | 0.86 | 0.77 | — | — |
| MMP-2 | 1.00 | 0.42 | 0.76 | 0.79 | 0.70 | 0.98 |
| MMP-9 | 1.00 | 0.58 | 0.79 | 0.79 | 1.10 | 0.95 |

EXAMPLE 7

Effects of Astragaloside Compounds on MMP and Collagen Expression Induced by PMA or IL-1β in Human Chondrocytes (HCHs)

Primary HCHs were cultured in chondrocyte growth medium (C-27101, PromoCell, GmbH, Heidelberg, Germany). The medium was supplemented with 10% FBS, 100 IU/mL penicillin, 100 µg/mL of streptomycin. The cells from passages 4 to 10 were used for this study. Culture medium was replaced every other day. After confluence, the cells were subcultured following trypsinization. For subculturing, cells were harvested after a brief treatment with 0.1% trypsin/EDTA solution and seeded at a dilution of 1:10. The cells were seeded at $1\times10^5$ cells in 6-well culture plate for 24 hours. At the beginning of the experiment, the cells were pre-treated with 100 ng/mL PMA or 10 ng/mL IL-1β for 24 hours. The cells were then treated with 0.1 µM Dexamethasone, various astragaloside compounds (0.1 µM) or extracts of *Astragalus membranaceous* (1 µg/mL) at indicated dosages for another 48 hours. For control sample, 0.1% DMSO was used as a negative control for these experiments. Control cultures were maintained in medium supplemented with 0.1% DMSO. No growth and differentiation effects of DMSO were observed under these culture conditions. The cell cultures finally were collected for western blotting analysis as described in Example 6.

As shown in the following Tables 7-9, the MMP expression induced by PMA or IL-1β in HCHs was inhibited by the astragaloside compounds of the present invention, so that both cytoplasmic and secreted MMP levels were reduced. In addition, the level of secreted Type II collagen, which is a collagen specific to chondrocytes, was increased. These results together indicate that the astragaloside compounds of the present invention not only reduce tissue damage by inflammation due to the release of MMPs, but also enhance the expression of collagen to protect chondrocytes from damage.

TABLE 7

Western blot results (PMA-pre-treated HCH cell extract)

| | Ctrl | AS6 | AA |
|---|---|---|---|
| MMP-1 | 1.00 | NA | 0.44 |
| MMP-13 | 1.00 | 0.54 | 0.44 |

NA: non-available.

TABLE 8

Western blot results (PMA-pre-treated HCH culture medium)

| | Ctrl | Dex | AS6 | AA |
|---|---|---|---|---|
| MMP-1 | 1.00 | 0.28 | 0.51 | 0.44 |
| MMP-13 | 1.00 | 0.74 | 0.26 | 0.49 |
| Type II Collagen | 1.00 | 1.20 | 1.74 | 1.42 |

TABLE 9

Western blot results (IL-1β-pre-treated HCH culture medium)

| | Ctrl | Dex | AS3 | AS4 | AS6 | AS water insoluble fraction | AS ethanol fraction |
|---|---|---|---|---|---|---|---|
| MMP-1 | 1.00 | 0.28 | — | — | 0.97 | 0.25 | 0.76 |
| MMP-13 | 1.00 | 0.74 | 0.75 | 0.55 | — | 0.69 | 0.56 |
| Type II Collagen | 1.00 | 1.20 | 1.03 | 1.16 | 1.34 | 1.12 | 0.98 |

EXAMPLE 8

Effects of Astragaloside Compounds on Glucosamine and Proline Uptake in HCHs\

Glucosamine Uptake Assay

The HCHs were cultured as described above in Example 7. For the glucosamine uptake test, HCH cells were seeded into 24-well plate at a density of $3\times10^4$ cells per well and cultured for 24 hours. The cells were then treated in the absence (solvent control) or presence of the astragalosides (0.1 µM) or *Astragalus membranaceous* extracts (1.0 µg/mL) for another 24 hours. The treated cells were then washed twice with PBS and incubated in glucose and serum free medium (GSFM). After 2 hours, the cells were replaced with fresh GSFM containing 0.2 µCi of [$^{14}$C]-Glucosamine (American Radiolabelled Chemicals Inc, ARC, St. Louis, Mo., USA). At the designated time interval, the cells were washed twice with GSFM containing cold glucosamine and then lysed in 200 µL of 2% SDS. Cell lysates were centrifuged at 15000 g for 15 min. Intracellular uptaken glucosamine was determined by transferring 10 µL of the cell lysate to filter-bottomed UniFilter plates (Perkim-Elmer) and counting. The samples were measured for their protein concentration using the BCA protein assay kit as described above. The amount of glucosamine accumulated in the cells was calculated and normalized to protein concentration and uptake rate was expressed as counts per minute per microgram of cell protein (cpm/min/µg).

Figure 6:
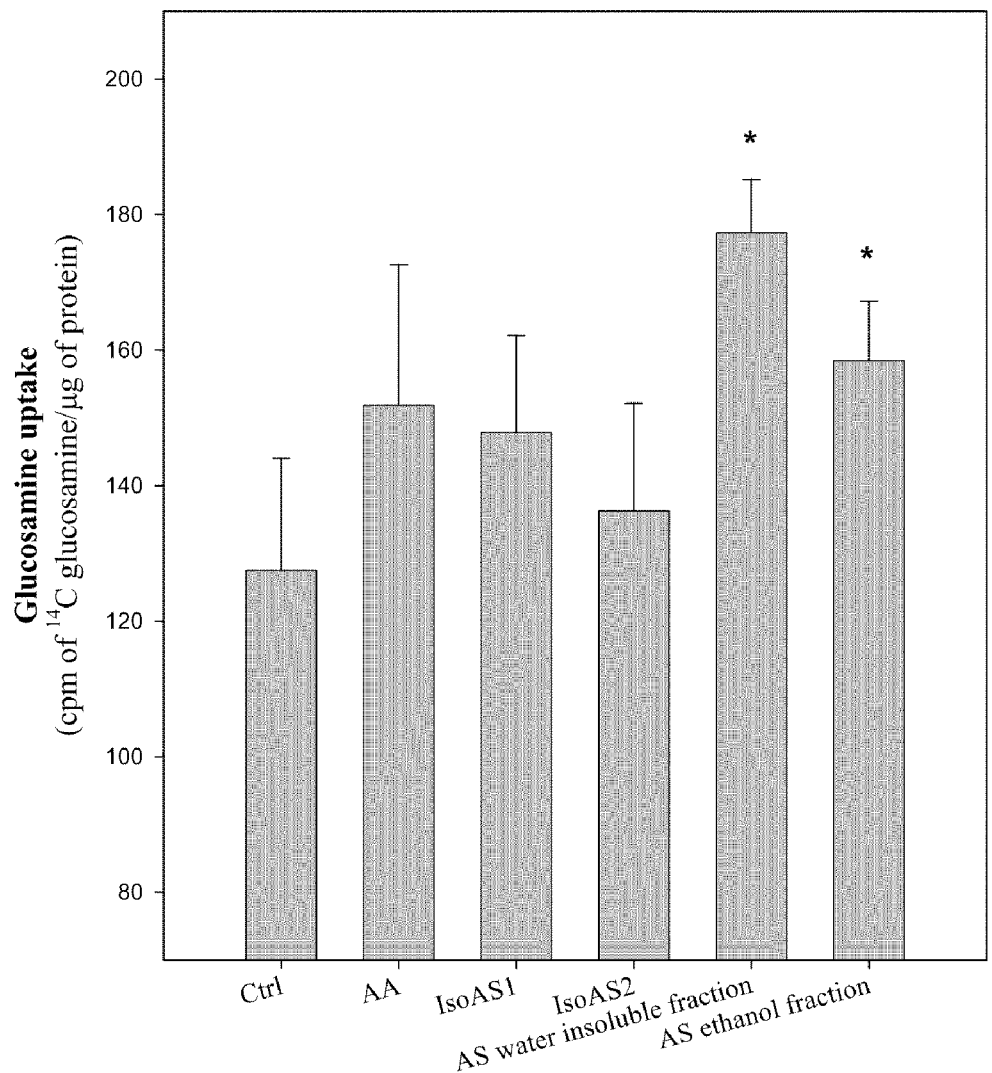
FIG. 6 is a diagram showing the result of the glucosamine uptake assay. "Ctrl" refers to the control group; "AS water insoluble fraction" refers to the *Astragalus membranaceous* extract obtained by first extracting *Astragalus membranaceous* with ethanol, followed by extracting the alcohol extract with water; and "AS ethanol fraction" refers to the *Astragalus membranaceous* extract obtained by extracting *Astragalus membranaceous* with ethanol. * indicates $p<0.05$.

Glucosamine is the primary building block of hyaluronic acid (HA), which is a protective substance in tissue. A measurement of glucosamine uptake by the cells suggests synthesis of HA in human cells. As shown in the following Table 10 and FIG. 6, the astragaloside compounds of the present invention enhanced glucosamine uptake by chondrocytes, thereby increasing HA synthesis and providing a protective effect to the cartilage tissue.

TABLE 10

Results of the glucosamine uptake assay

| | Ctrl | AA | IsoAS1 | IsoAS2 | AS water insoluble fraction | AS ethanol fraction |
|---|---|---|---|---|---|---|
| Relative fold | 1.00 | 1.19 | 1.16 | 1.07 | 1.39 | 1.24 |

Proline Uptake Assay

The proline uptake assay was carried out as described below, generally in accordance with the method disclosed in *Biochim Biophys Acta.* 1104:283-292, 1992, the contents of which are incorporated by reference. Briefly, HCH cells were seeded into a 24-well plate at a density of $3 \times 10^4$ cells per well and cultured for 24 hours. The cells were then treated in the absence (solvent control) or presence of the astragalosides (0.1 µM) or *Astragalus membranaceous* extracts (1.0 µg/mL) for another 24 hours. The treated cells were then washed once with PBS and incubated in amino acid free medium (AAFM) for another 30 min. The treated cells were then replaced with fresh AAFM containing 50 µg/mL of ascorbate and total of 0.5 mM of L-proline containing 1 µCi [$^3$H] Proline (American Radiolabelled Chemicals Inc, ARC, St. Louis, Mo., USA). At designated time intervals, the cells were washed with AAFM containing cold proline and then lysed in 200 µL of 2% SDS. Cell lysates were centrifuged at 15000 g for 15 min. Intracellular proline uptaken by the cells was determined by transferring 10 µL of the cell lysate to filter-bottomed UniFilter plates (Perkim-Elmer) and counting. The samples were measured for their protein concentrations using the BCA protein assay kit as described above. The amount of proline accumulated in the cells was calculated and normalized to protein concentration. And cellular uptake rate was expressed as nmole of L-proline per minute per milligram of cell protein (nmole/min/µg).

Figure 7:
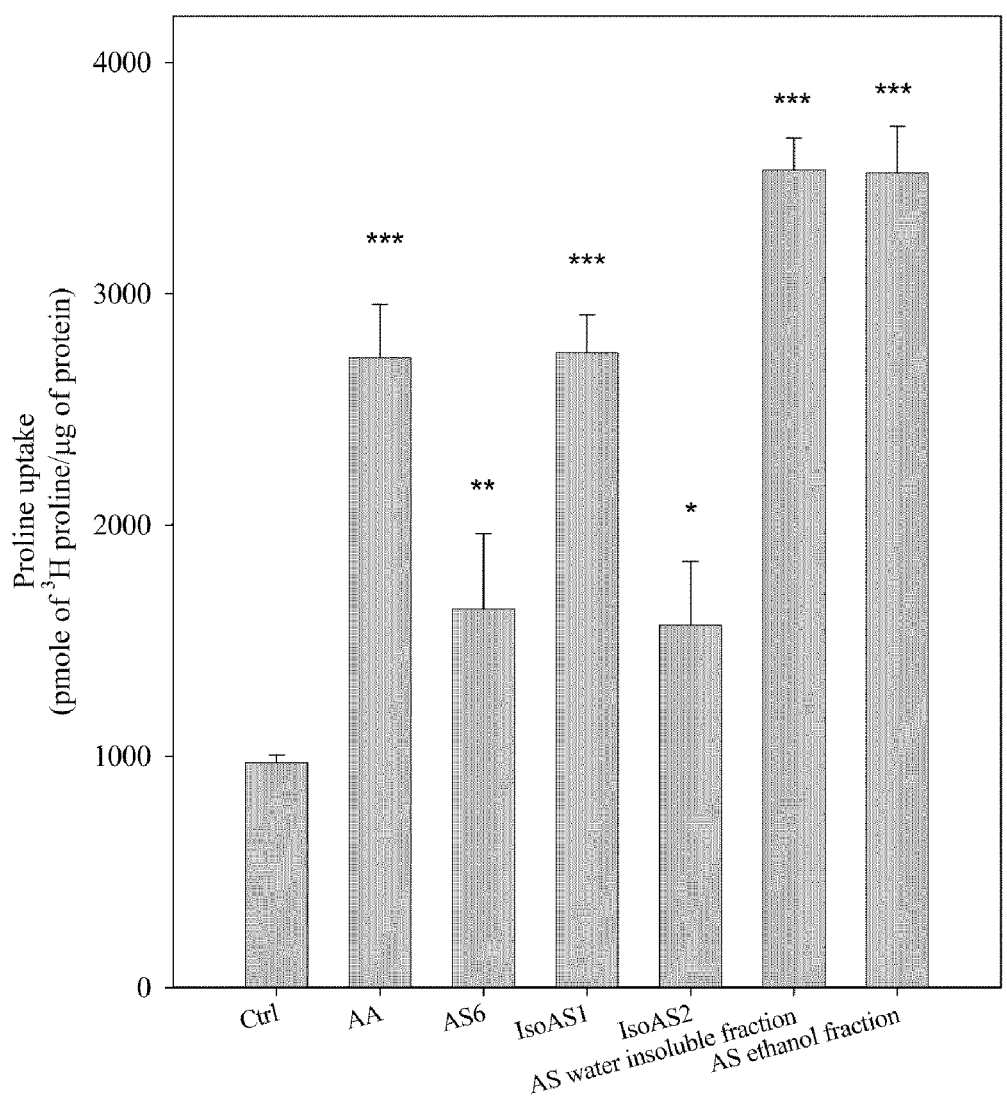
FIG. 7 is a diagram showing the result of the proline uptake assay. "Ctrl" refers to the control group; "AS water insoluble fraction" refers to the *Astragalus membranaceous* extract obtained by first extracting *Astragalus membranaceous* with ethanol, followed by extracting the alcohol extract with water; and "AS ethanol fraction" refers to the *Astragalus membranaceous* extract obtained by extracting *Astragalus membranaceous* with ethanol. * indicates $p<0.05$,  indicates $p<0.01$, * indicates $p<0.005$.

Proline is an amino acid necessary for the synthesis of collagen. A measurement of proline uptake by the cells indicates increased potential of collagen synthesis in the cells. As shown in the following Table 11 and FIG. 7, the astragaloside compounds of the present invention enhanced proline uptake by chondrocytes, thereby enhancing their potential of collagen synthesis. Such results suggest that the astragaloside compounds of the present invention are useful in preventing cartilage degeneration and treating cartilage damaged by inflammation.

TABLE 11

Results of the proline uptake assay

| | Ctrl | AA | AS6 | IsoAS1 | IsoAS2 | AS water insoluble fraction | AS ethanol fraction |
|---|---|---|---|---|---|---|---|
| Relative fold | 1.00 | 2.80 | 1.69 | 2.82 | 1.61 | 3.64 | 3.63 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of treating a disease associated with cartilage defect which is caused by an increased level of matrix metalloproteinase 1 in an articular site, said method comprising administering to a subject in need thereof a cycloartane compound of Formula I at an amount effective to decrease the level of matrix metalloproteinase 1:

Formula I wherein
  $R_1$ is H, OH, O-acetyl, O-xylopyranosyl, O-(2-actetylxylopyranosyl), O-(3-actetylxylopyranosyl), O-(2,3-diactetylxylopyranosyl), O-(2,4-diactetylxylopyranosyl), O-(2,3,4-triactetylxylopyranosyl), O-xylopyranosyl-(1-2)-β-D-glucopyranosyl, or O-xylopyranosyl-(1-2)-α-D-arabinopyranosyl;
  $R_2$ is H, OH, O-acetyl, O-glucopyranosyl, or O-xylopyranosyl;
  $R_3$ is H, OH, and O-acetyl; and
  $R_4$ is 2. The method of claim 1, wherein the cycloartane compound is contained in an alcoholic extract of the rhizome of *Astragalus membranaceous*.

3. The method of claim 2, wherein the alcoholic extract is an ethanolic extract.

4. The method of claim 2, wherein the alcoholic extract of *Astragalus membranaceous* is prepared by a process including (i) exacting *Astragalus membranaceous* with ethanol, (ii) collecting an ethanol-soluble fraction, (iii) extracting the ethanol-soluble fraction with water, and (iv) collecting a water-insoluble fraction.

5. The method of claim 1, wherein the cycloartane compound is a compound of Formula II:

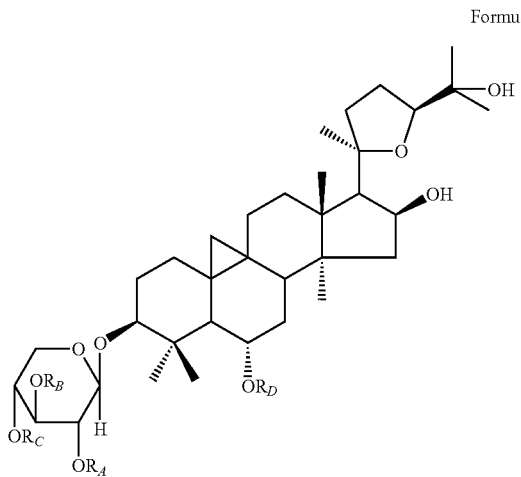

Formula II in which $R_A$ is H, acetyl (Ac) or glucopyranoside (Glc); each of $R_B$ and $R_C$, independently, is Ac or H; and $R_D$ is H, Ac, or Glc.

6. The method of claim 5, wherein $R_A$ is Ac, $R_B$ is Ac, $R_C$ is H, and $R_D$ is Glc.

7. The method of claim 5, wherein $R_A$ is Ac, $R_B$ is H, $R_C$ is H, and $R_D$ is Glc.

8. The method of claim 5, wherein $R_A$ is Glc, $R_B$ is H, $R_C$ is H, and $R_D$ is H.

9. The method of claim 5, wherein $R_A$ is H, $R_B$ is H, $R_C$ is H, and $R_D$ is Glc.

10. The method of claim 5, wherein $R_A$ is Glc, $R_B$ is H, $R_C$ is H, and $R_D$ is Glc.

11. The method of claim 5, wherein $R_A$ is Ac, $R_B$ is H, $R_C$ is Ac, and $R_D$ is Glc.

12. The method of claim 5, wherein $R_A$ is H, $R_B$ is Ac, $R_C$ is H, and $R_D$ is Glc.

13. The method of claim 1, wherein $R_1$ is OH, $R_2$ is O-glucopyranosyl, $R_3$ is OH, and $R_4$ is

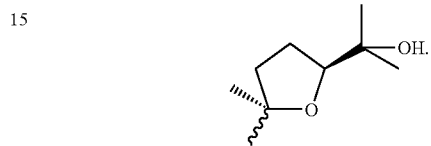

14. The method of claim 1, wherein the cycloartane compound is administered orally.

15. The method according to claim 1, wherein the cycloartane compound is administrated intra-articularly to an arthritic joint area.

16. The method of claim 1, wherein the disease is degenerative arthritis.

* * * * *